(12) United States Patent
McNeal et al.

(10) Patent No.: US 8,316,470 B2
(45) Date of Patent: Nov. 27, 2012

(54) EYEWEAR LENS ATTACHMENT SYSTEM AND METHOD

(75) Inventors: Joseph R. McNeal, Hailey, ID (US); George T. Giroux, Ketchum, ID (US)

(73) Assignee: Smith Optics, Inc., Ketchum, ID (US)

( * ) Notice: Subject to any disclaimer, the term of this patent is extended or adjusted under 35 U.S.C. 154(b) by 858 days.

(21) Appl. No.: 11/836,729

(22) Filed: Aug. 9, 2007

(65) Prior Publication Data

US 2009/0038059 A1   Feb. 12, 2009

(51) Int. Cl.
*A61F 9/02* (2006.01)

(52) U.S. Cl. .................................. 2/438; 2/448

(58) Field of Classification Search .............. 2/438, 439, 2/448, 451
See application file for complete search history.

(56) References Cited

U.S. PATENT DOCUMENTS

| | | | | |
|---|---|---|---|---|
| 2,423,539 A * | 7/1947 | Williams | ........................ | 351/44 |
| 2,864,088 A * | 12/1958 | Gongoll | ............................ | 2/441 |
| 3,718,937 A * | 3/1973 | Smith | ................................ | 2/436 |
| 3,945,044 A | 3/1976 | McGee et al. | ................. | 2/14 H |
| 5,802,622 A | 9/1998 | Baharad et al. | .................... | 2/434 |
| 6,047,410 A | 4/2000 | Dondero | ............................ | 2/426 |
| 6,349,420 B1 | 2/2002 | Chiang | ............... | 2/428 |
| 6,637,877 B1 * | 10/2003 | Hartley et al. | .................. | 351/44 |
| 6,948,813 B2 * | 9/2005 | Parks | ............................ | 351/158 |
| 7,011,404 B2 * | 3/2006 | Howard et al. | ................. | 351/83 |
| D552,662 S | 10/2007 | Woxing | | |
| 7,497,569 B2 * | 3/2009 | Webb | ............................ | 351/106 |
| 7,681,257 B1 * | 3/2010 | Broersma | ........................ | 2/425 |
| 2004/0221375 A1 * | 11/2004 | Douglas | ............................ | 2/424 |
| 2007/0033718 A1 | 2/2007 | Lin | ................................. | 2/448 |
| 2007/0153230 A1 * | 7/2007 | Musal et al. | .................. | 351/142 |

FOREIGN PATENT DOCUMENTS

WO    WO-2009/023491 A2    2/2009

OTHER PUBLICATIONS

International Search Report & Written Opinion dated Jan. 29, 2009 for PCT Appl. No. PCT/US2008/072332.

* cited by examiner

*Primary Examiner* — Katherine Moran
(74) *Attorney, Agent, or Firm* — Dorsey & Whitney LLP (57) ABSTRACT

A goggle is disclosed having a frame with upper and lower frame portions with the upper frame portion being substantially more rigid than the lower frame portion. A fastener secures the upper perimeter of a lens to the upper frame portion. The lower portion includes slots receiving tabs extending from opposing sides of a notch in the lens for receiving the wearer's nose. The fastener includes an elongate member insertable within a slot formed in the lens and rotatable to a crosswise position hindering removal of the elongate member from the slot.

42 Claims, 6 Drawing Sheets

EYEWEAR LENS ATTACHMENT SYSTEM AND METHOD

TECHNICAL FIELD

This invention relates generally to ski goggles, and more specifically to methods and apparatus for removably securing a lens to a goggle frame.

BACKGROUND OF THE INVENTION

Goggles are widely used in a variety of applications, such as when skiing and snowboarding, working in hazardous conditions or with hazardous substances. Goggles typically include a frame having a somewhat oval configuration with an inner edge adapted to contact a wearer's face, often through a cushioning foam face gasket. The frame usually has an arcuate shape curving rearwardly at the sides to conform to a wearer's face. A lens is normally mounted in the frame near or at an outer edge of the frame so that the lens and wearer's face substantially enclose the interior of the frame. The goggle is normally held on the wearer's head by an elastic headband having its ends attached to opposite side edges of the goggle frame. The headband may be attached directly to the goggle frame, or it may be attached through an intervening structure.

The lenses of modern goggles are often tinted to shield the wearer's eyes from the glare from the snow. However, the level of light reduction needed depends on weather conditions and the time of day. In cloudy conditions less glare reduction is needed and the wavelengths that need to be filtered by the lens may be different. Likewise, when night skiing it may be desirable to have no tinting whatsoever.

The lens provided with goggles may also become inadequate as they are scratched or otherwise damaged. For example, some lenses have metallicized coatings that are easily scratched.

In view of the foregoing it would be an advancement in the art to provide a ski goggle having a readily replaceable lens in order to enable a user to use different lenses having an appropriate level of glare reduction without the need for multiple goggles. Such a replaceable lens would further enable replacement of damaged lenses without the need to purchase an additional goggle frame.

SUMMARY OF THE INVENTION

In one aspect of the invention, a goggle includes a lens having right and left eye portions. A frame is selectively engaged with a perimeter of the lens and includes an upper portion extending across an upper perimeter of the right and left eye portions and a lower portion extending across a lower perimeter of the right and left eye portions. One of the upper and lower portions is substantially more rigid than the other of the upper and lower portions and has at least one fastener secured thereto. The fastener selectively engages the lens to retain the lens in engagement with the frame.

In another aspect of the invention, the fastener includes a latch pivotally coupled to one of the upper and lower frame portions. The latch is selectively pivotable between a first position in which the latch retains the lens with respect to the frame and a second position in which the latch permits the lens to be removed from the frame.

In another aspect of the invention, the lens defines a slot extending therethrough. The latch includes an elongate member mounted on a shaft secured to the frame. The elongate member is rotatable within the slot to a crosswise position in which the slot interferes with removal of the elongate member from the slot.

In another aspect of the invention a plate secures to the elongate member having a portion of the lens positioned between the plate and the frame when the latch is in the first position.

In another aspect of the invention, an over-center mechanism engages the latch, the over-center mechanism biases the latch away from an intermediate position between the first and second positions and resists movement of the latch between the first and second positions.

In another aspect of the invention strap mounts secured to the frame, each having first and second ends and an intermediate portion extending between the first and second ends. The first ends secure to the upper frame portion and the lower ends secure to the lower frame portion. The strap secures to the intermediate portion such that the intermediate portion urges the lens against the frame upon tensioning of the strap.

DETAILED DESCRIPTION OF PREFERRED EMBODIMENTS

Figure 1:
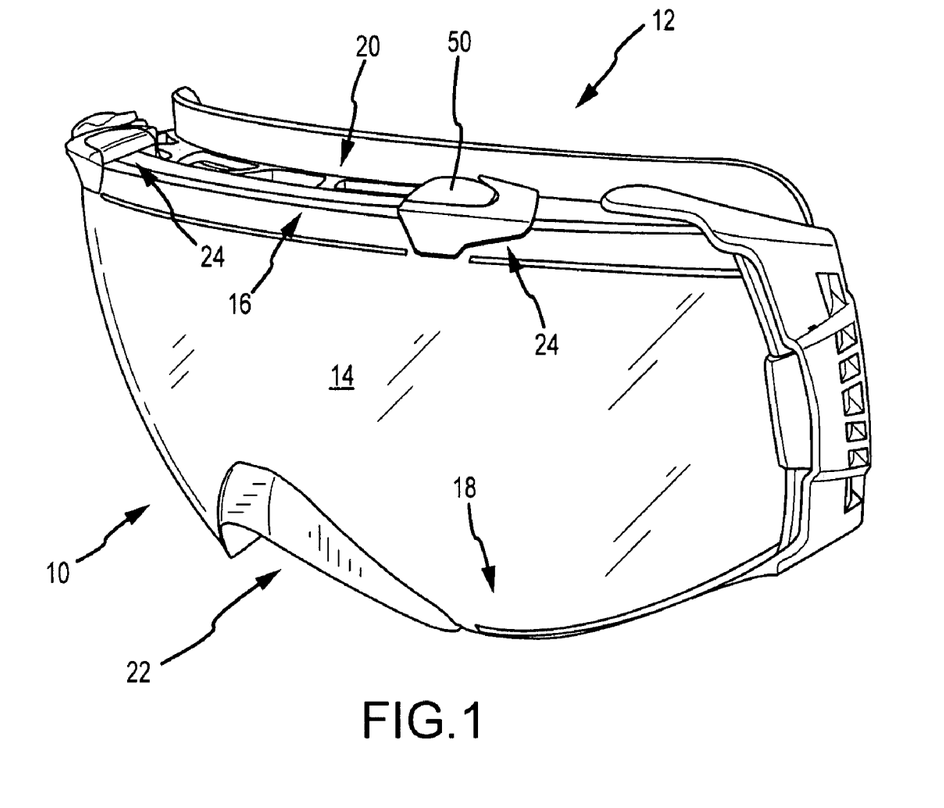
FIG. 1 is an isometric view of a goggle having a removable lens in accordance with an embodiment of the present invention.

Referring to FIG. 1, a goggle 10 includes a frame 12 and a lens 14 secured to the frame 12. The lens 14 includes an upper perimeter 16 and a lower perimeter 18 engaging an upper portion 20 and lower portion 22, respectively, of the frame. One or more fasteners 24 are secured to one of the upper and lower portions 20, 22 for securing the lens 14 to the frame 12. For example, in the illustrated embodiment, the fasteners 24 are secured to the upper portion 20 of the frame 12 which is substantially more rigid than the lower portion 22. The fasteners 24 are preferably manually releasable to enable ready assembly and disassembly of the lens 14 and frame 12. The portion 20, 22 to which the fastener 24 secures may be relatively rigid as compared to the other portion 20, 22. In some embodiments, a stiffening member is provided within the more rigid portion 20, 22. The stiffening member may be fastened to the more rigid portion 20, 22, or be integrally or monolithically formed with the more rigid portion 20, 22.

In an alternative embodiment, the frame portions 20, 22 may be of the same or dissimilar stiffness. In such embodiments, four fasteners 24 may be used, two mounted to the upper portion 20 and two mounted to the lower portion 22. In other alternative embodiments, the goggle 10 is replaced by sunglasses having two lenses 14 mounted to the frame 12. The sunglasses may include two fasteners 24 one selectively engaging each lens near the top, bottom, or sides, of the lens. Alternatively, each lens may be inserted in the frame and selectively engage two fasteners 24 mounted to the frame, one at the top and bottom, or one either side, of each lens.

Figure 2:
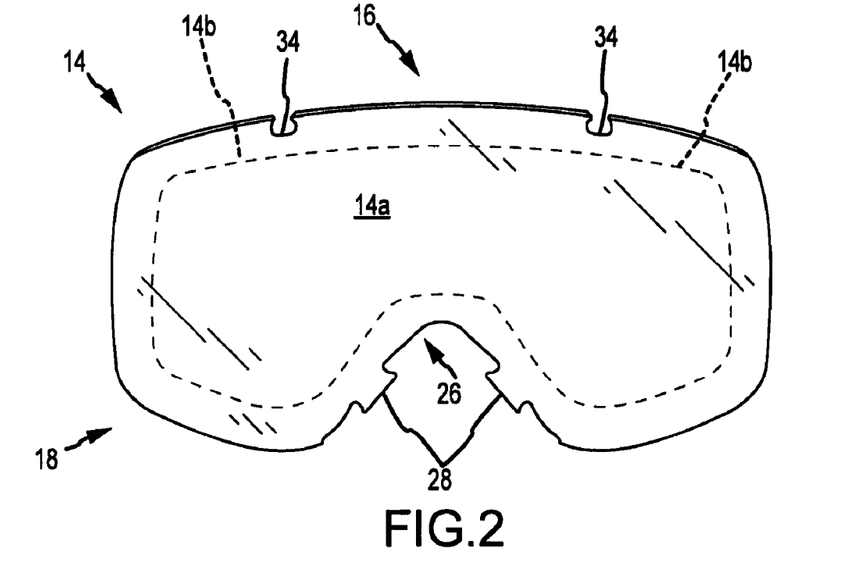
FIG. 2 is a front plan view of a removable lens in accordance with an embodiment of the present invention.

Referring to FIG. 2, a notch 26 for receiving the wearer's nose is formed in the lower perimeter 18 of the lens 14 between right and left eye portions of the lens 14. Tabs 28 are formed on opposing faces of the notch 26 for removably securing the lens 14 to the lower portion 22 of the frame 12.

Figure 3A:
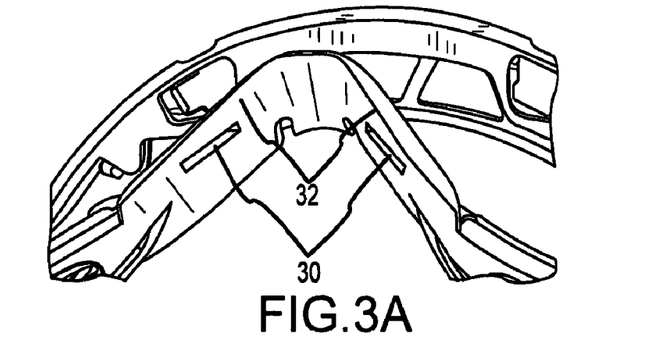
FIGS. 3A and 3B are isometric views of a latching mechanism for securing the removable lens to the lower portion of a goggle frame in accordance with an embodiment of the present invention.
Figure 3B:
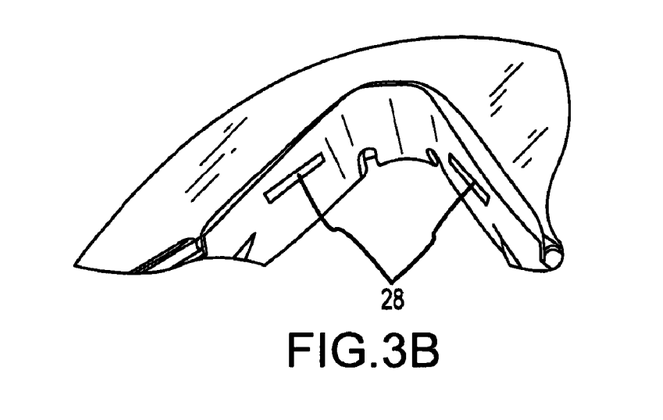

Referring to FIGS. 3A and 3B, while still referring to FIGS. 1 and 2, the tabs 28 are inserted within slots 30 formed in the lower portion 22. Specifically, the slots 30 are formed in angled members 32 disposed to be supported by the nose of the wearer. The angled members 32 are typically flexible and/or flexibly secured to one another or to the rest of the frame such that the angled members 32 may deflect to allow the tabs 28 to be inserted within the slots 30 and removed from the slots 30. In an alternative embodiment, tabs formed on the angled members 32 engage slots or recesses formed in the lower perimeter 18 of the lens 14. Other fastening means may also be used.

Referring again to FIG. 2, slots 34 may be formed in the upper perimeter 16 of the lens 14 for engaging the fastener 24. In other embodiments, slots 34 are formed in the lower perimeter 18, or in both the upper and lower perimeters 16, 18 and engage fasteners 24 mounted on the upper and lower frame portions 20, 22 that have the same or dissimilar stiffness. In one method of use, the lower perimeter 18 is secured to the lower portion 22 of the frame 12. The lower portion 22 of the frame 12 with the lens 14 attached is then deflected away from the upper portion 20 of the frame 12 in order to position the slots 34 below the fastener 24. The lower portion 22 and lens 14 are then deflected toward the upper portion 20, which brings the slots 34 into engagement with the fastener 24. The fastener 24 may then be transitioned to a locked state in which the upper perimeter 16 of the lens 14 is retained against the upper portion 20 of the frame 12.

In some embodiments, the lens 14 includes a first lens 14a and a second lens 14b defining a closed volume between them to provide insulation between the outside air and air trapped between the goggle 10 and the wearer's face. In such embodiments, the second lens 14b may be smaller than the first lens 14a such that the slots 34 are formed in a portion of the second lens extending outwardly from the perimeter of the second lens 14b. The tabs 28 may likewise be formed in a portion of the first lens 14a extending outwardly from the perimeter of the second lens 14b.

In the illustrated embodiment, the second lens 14b is sized to be inserted within the frame 12 whereas the rear surface of the first lens 14a is pressed against the face of the frame 12, with the exception of the notch 26, which may be received by grooves formed in the angled members 32, as shown in FIG. 1.

Figure 4:
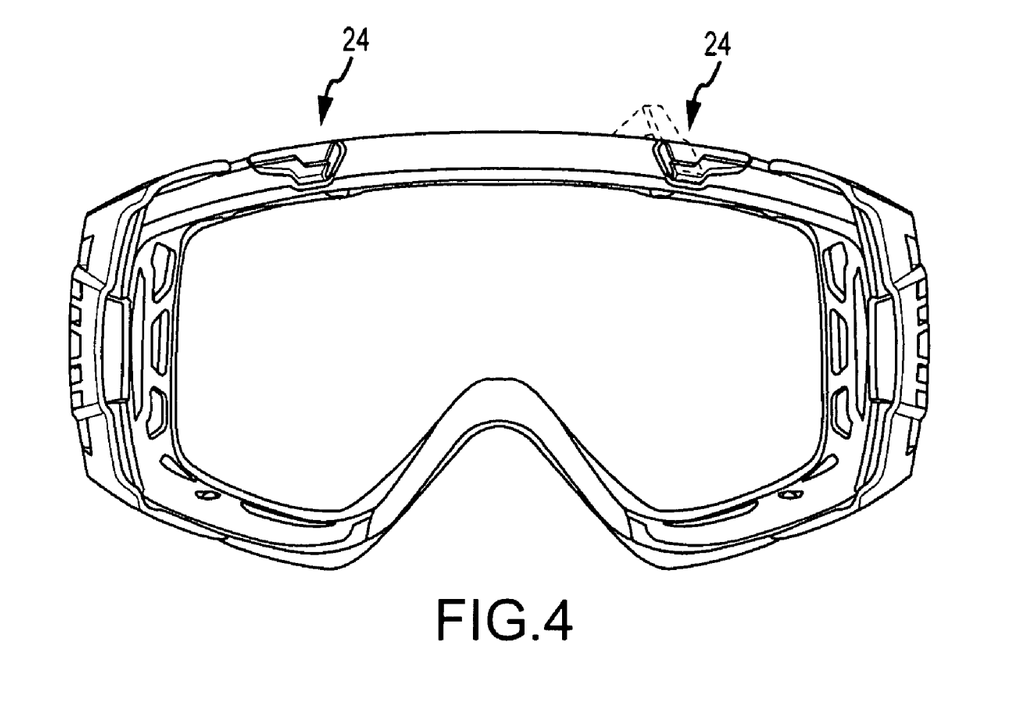
FIG. 4 is a front elevation view of a frame suitable for receiving a removable lens in accordance with an embodiment of the present invention.

Referring to FIG. 4, in the illustrated embodiment the fastener 24 is pivotally secured to the upper portion 20 of the frame 12. The fastener 24 may have an open position, shown in dotted lines, wherein the slots 34 can be moved freely into and out of engagement with the fastener. The fastener 24 also has a closed position wherein the lens 14 is retained by the fastener.

Figure 5:
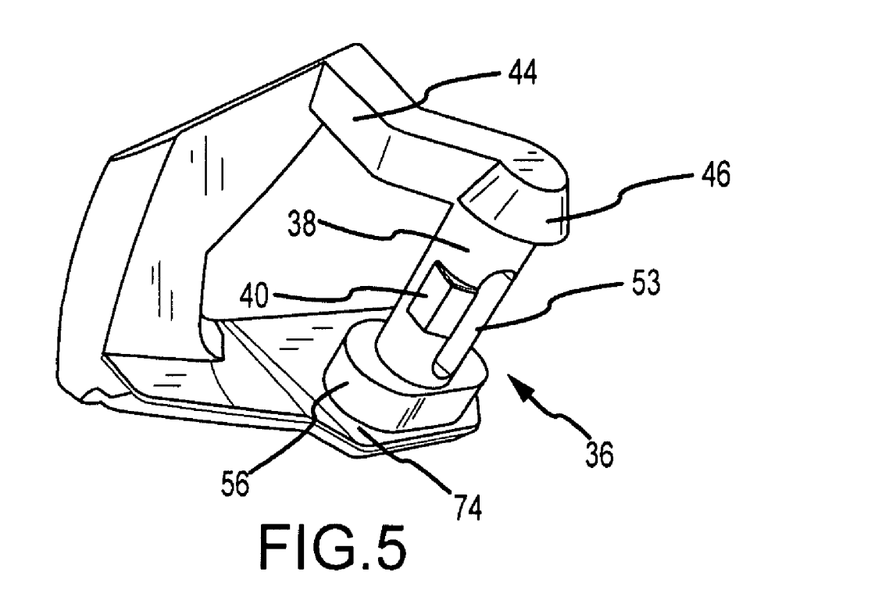
FIG. 5 is an isometric view of a pivoting latch in accordance with an embodiment of the present invention.
Figure 6:
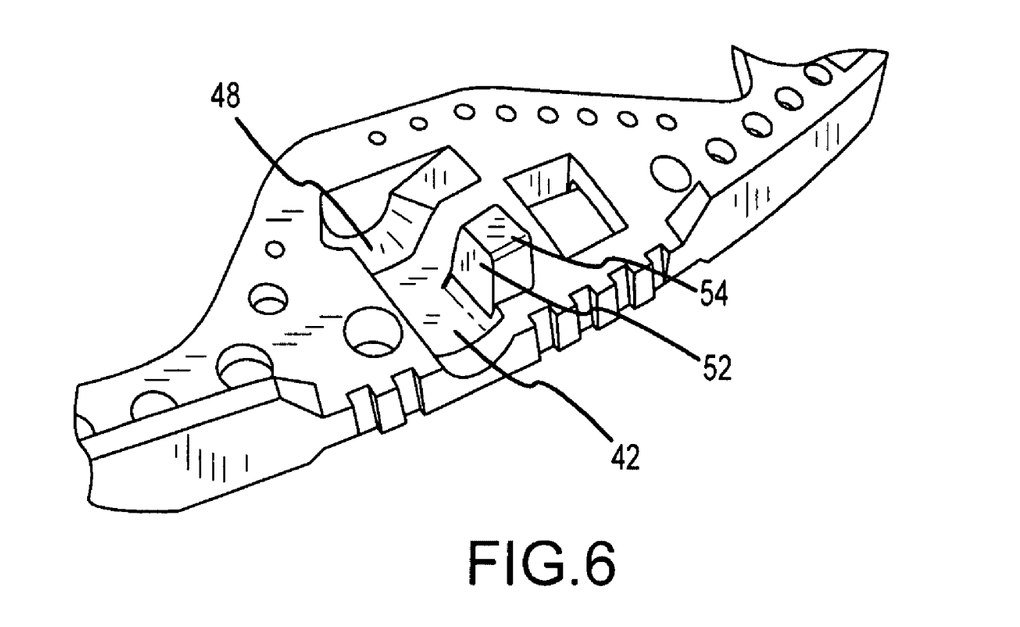
FIG. 6 is an isometric view of a seat for receiving a pivoting latch in accordance with an embodiment of the present invention.

Referring to FIGS. 5 and 6, in some embodiments the fasteners 24 each have an over-center mechanism 36 such that the fastener 24 is biased away from an intermediate position between the open and closed positions. In the illustrated embodiment, the over-center mechanism 36 includes a shaft 38 bearing a projection 40. Other over-center mechanisms 36 known in the art may also be used. The illustrated shaft 38 is pivotally mounted to the frame, such as by means of a seat 42 formed on or secured to the frame. The shaft 38 may be secured to an arm 44 enabling a user to rotate the shaft 38. In the illustrated embodiment, a cap 46 is secured to the shaft 38 and fits within a recess 48 such that the shaft 38 resists removal along the longitudinal axis of the shaft. The shaft 38 may be retained within the seat 42 by a retaining member 50 fastened to the frame 12 over the seat 42. (See FIGS. 1 and 9).

Figure 7A:
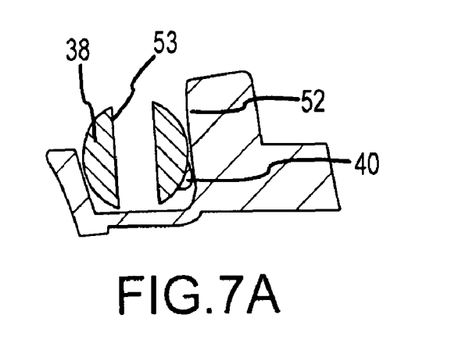
FIGS. 7A and 7B are cross-sectional views showing an over-center mechanism suitable for use with the pivoting latch of FIG. 5 in accordance with an embodiment of the present invention.
Figure 7B:
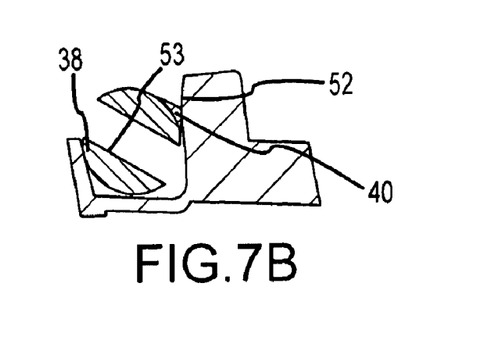

Referring to FIGS. 7A and 7B, while still referring to FIGS. 5 and 6, the projection 40 engages a surface 52 fixedly secured to the frame 12. In the illustrated embodiment, the surface 52 is formed on a post 54 extending upwardly from the seat 42.

As shown in FIG. 7A, in one position, the projection 40 is located to one side of the point where the shaft 38 and surface 52 are closest to one another, whereas in FIG. 7B, the projection is located on the opposite side. In order to move between the orientations of FIGS. 7A and 7B, the projection 40 must move across the surface 52. This requires either the surface 52 or shaft 38 to resiliently deflect, providing the biasing force urging the shaft 38 toward either the open or closed position. In the illustrated embodiment, the shaft 38 includes a slot 53 facilitating bending of the shaft 38 when transitioning between the open and closed positions.

Figure 8A:
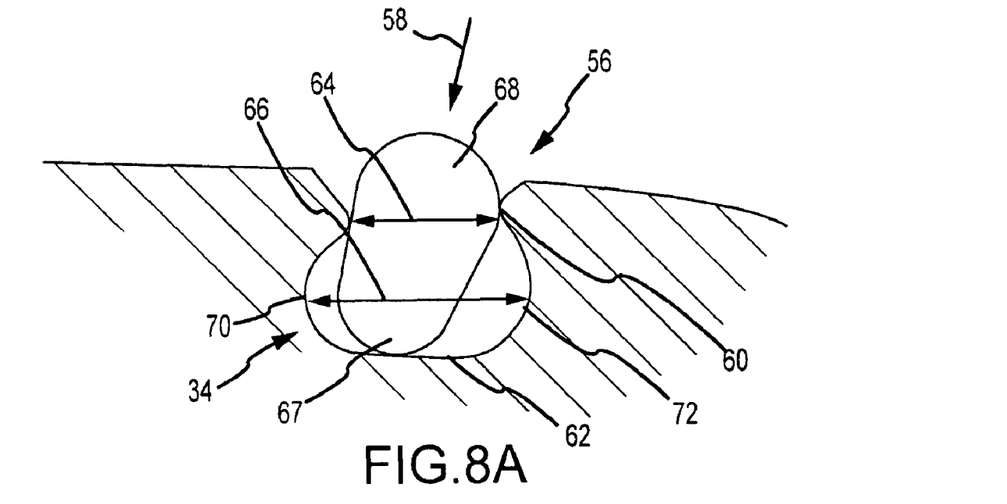
FIGS. 8A and 8B are side cross-sectional views of a fastener for securing the removable lens to the upper portion of the frame in accordance with an embodiment of the present invention.
Figure 8B:
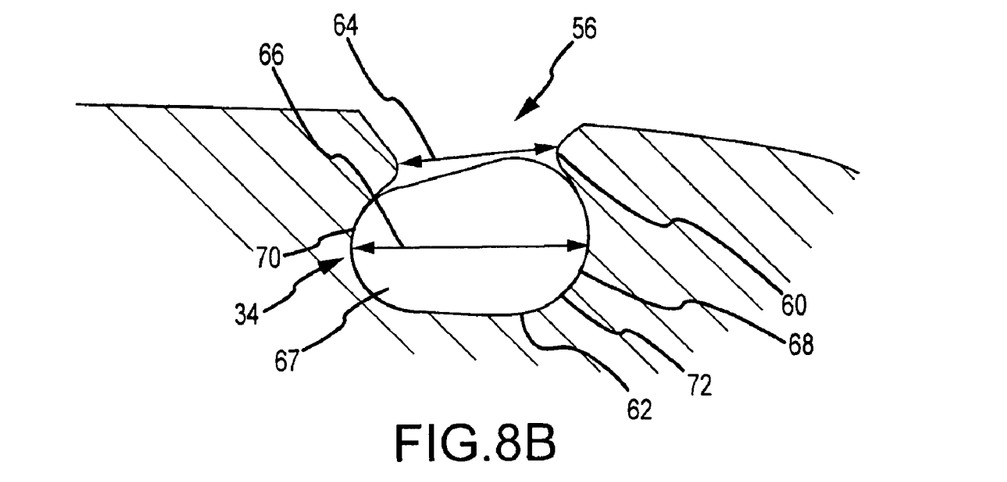

Referring to FIGS. 8A and 8B, while still referring to FIGS. 5 and 6, the fasteners 24 may each include an elongate member 56 secured to the shaft 38 having its direction of elongation perpendicular to the axis of rotation and/or longitudinal axis of the shaft. In the open position, the elongate member 56 is oriented relative to the slot 34 such that the elongate member 56 may be inserted along an insertion direction 58 through an opening 60 of the slot 34 that extends from the perimeter of the lens 14 to a widened portion 62 having a width 64 substantially greater than the width 66 of the opening. The width 64 is typically such that the elongate member 56 may be rotated into the closed position shown in FIG. 8B within the widened portion 62.

In some embodiments, the elongate member 56 is formed of a resilient material such that the width 64 is smaller than the length of the elongate member 56 along its direction of elongation and must therefore be deformed to achieve the orientation of FIG. 8B. As is apparent in FIG. 8B, in the closed position the slot 34 interferes with movement of the elongate member 56 along the insertion direction to a greater extent than in the open position shown in FIG. 8A. In some embodiments, the elongate member 56 must deform in order to transition from the open position to the closed position. In the illustrated embodiment, the elongate member 56 includes a narrow end 67 and widened end 68. In such embodiments, the slot 34 may likewise include a narrow end 70 and a widened end 72. In the illustrated embodiment, the narrow end 67 is inserted first. As the elongate member 56 is rotated, the narrow end 67 draws the lens 14 upward toward the fastener 24 and the upper portion 20. The widened end 68 slides along the slot 34, deforming slightly, and then seats in the widened end 72 of the slot 34. The deformation required to remove the elongate member 56 from the slot 34 thereafter serves to retain it in the slot 34. The over-center mechanism 36 also hinders rotation of the elongate member 56 out of the slot 34.

Referring again to FIG. 4, while still referring to FIGS. 8A and 8B, in some embodiments, the elongate members 56 of the two fasteners 24 have opposite orientations such that they rotated in opposite directions when moving between the open and closed position. Accordingly, the arms 44 secured to the shafts 38 may be mirrored as illustrated in FIG. 4.

Referring again to FIGS. 5 and 6, the engagement of the elongate member 56 with the slot 34 may cooperate with a plate 74 to fasten the lens 14 to the frame. The plate 74 is secured to the shaft 38 or the elongate member 56 and captures the lens between itself and the frame 12 in order to prevent the slot 34 from sliding off the elongate member 56. In alternative embodiments, the plate 74 is not secured to the shaft 38 or elongate member 56, but rather is fixedly secured to the frame 12.

In one method of use, the lens 14 is first secured to the lower frame portion 22 as discussed above. The lower frame portion 22 and lens 14 are then moved away from the upper frame portion 20 by deflecting the lower frame portion 22 until the upper perimeter 16 of the lens 14 is positioned below the plates 74. The lens 14 is then moved upward between the plates 74 and the upper frame portion 20 and the elongate members 56 are inserted within the slots 34. The elongate members 56 are then rotated within the slot 34 as illustrated in FIGS. 8A and 8B to secure the upper perimeter 16 of the lens 14 to the upper frame portion 20.

Figure 9:
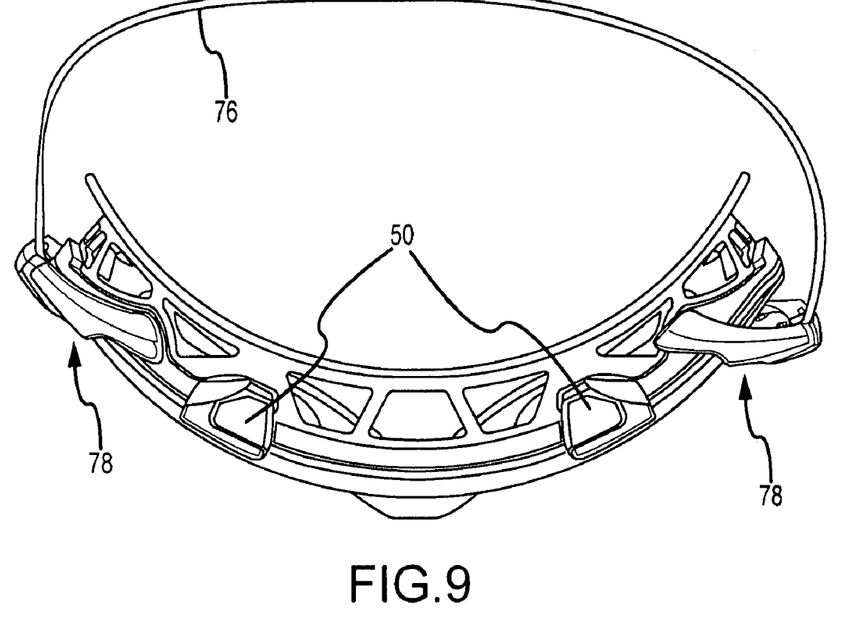
FIG. 9 is a top plan view of a frame and removable lens having pivoting strap mounts in accordance with an embodiment of the present invention.
Figure 10:
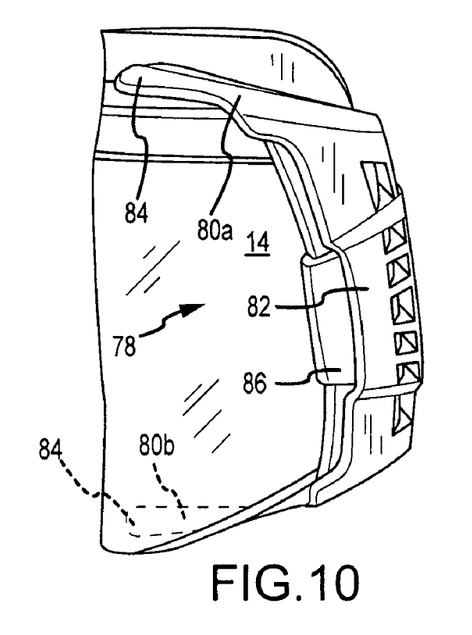
FIG. 10 is an isometric view of a pivoting strap mount in accordance with an embodiment of the present invention.

Referring to FIGS. 9 and 10, the goggle 10 includes a strap 76 for encircling the head of the wearer in order to retain the frame 12 against the face of the wearer. The strap 76 is preferably formed of an elastic material and is under tension when the goggle 10 is worn. The strap 76 may have an adjustable length.

The strap 76 is secured to the goggle 10 by means of strap mounts 78 secured on the right and left sides of the goggle. In some embodiments, the strap mounts 78 are pivotally mounted to the frame 12 and facilitate wearing of the goggle 10 by an individual wearing a helmet. For example, the strap mounts 78 may include arms 80*a*, 80*b* secured to the upper and lower frame portions 20, 22, respectively. An intermediate portion 82 extends between the arms 80*a*, 80*b*. The arms 80*a*, 80*b* pivotally secure to the upper and lower frame portions 20, 22, respectively, at points of securement 84 located inwardly from the right and left ends of the goggle 10. The intermediate portions 82 of the strap mounts 78 are located closer to the right and left ends, respectively, of the goggle 10 than the points of securement 84 such that when the strap 76 is secured to the intermediate portion 82 and tensioned the intermediate portion is urged against the lens 14. A pad 86 may be secured to the intermediate portion 82 such that the pad 86 is positioned between the intermediate portion 82 and the lens 14. The pad 86 is preferably formed of a resilient material such as a natural or synthetic rubber.

In use, the intermediate portion 82 is pivoted away from the frame 12 when the lens is inserted. After the lens 14 is positioned against the frame, the intermediate portion 82 is pivoted toward the lens and may serve to urge the lens 14 against the frame 12 when tension is applied to the strap 76.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A goggle comprising:
 a lens having right and left eye portions, the lens defining at least one slot;
 a frame selectively engaging a perimeter of the lens, the frame comprising an upper portion extending across an upper perimeter of the right and left eye portions and a lower portion extending across a lower perimeter of the right and left eye portions;
 a mounting structure disposed on one of the upper and lower portions, the combined mounting structure and the one of the upper and lower portions on which it is disposed being substantially more rigid than the other of the upper and lower portions;
 strap mounts pivotally mounted to the frame and a strap secured to the strap mounts; and
 a fastener disposed on the mounting structure and including a shaft rotatably secured to the frame, the shaft having a portion configured to be rotatable within the at least one slot and to selectively engage the at least one slot to retain the lens in engagement with the frame.

2. The goggle of claim 1, wherein the mounting structure is integrated with the frame.

3. The goggle of claim 1, wherein the fastener mounts to the upper portion.

4. The goggle of claim 1, wherein the fastener includes a latch pivotally coupled to one of the upper and lower frame portions, the latch selectively pivotable between a first position in which the latch retains the lens with respect to the frame and a second position in which the latch permits the lens to be removed from the frame.

5. The goggle of claim 4, wherein the latch includes an elongate member mounted to said shaft rotatably secured to the frame, the elongate member rotatable within the slot to a crosswise position in which the slot interferes with removal of the elongate member from the slot.

6. The goggle of claim 5, wherein the lens defines an opening extending from the perimeter of the lens to the slot, the slot being wider than the opening.

7. The goggle of claim 6, wherein the elongate member is insertable through the opening when the latch is in the second position and is not insertable through the opening when the latch is in the first position.

8. The goggle of claim 5, further comprising a plate secured to the elongate member, a portion of the lens positioned between the plate and the frame when the latch is in the first position.

9. The goggle of claim 5, wherein the lens includes first and second lenses secured to one another, the slot being formed in a portion of the second lens extending outwardly from a perimeter of the first lens.

10. The goggle of claim 9, wherein the perimeter of the first lens is sized to fit within an inner perimeter of the frame and wherein the second lens engages a face of the frame extending outwardly from the inner perimeter.

11. The goggle of claim 5, wherein the elongate member has first and second ends, the second end being wider than the first end.

12. The goggle of claim 4, wherein the latch is a first latch, the fastener further comprising a second latch pivotally coupled to one of the upper and lower portions offset from the first latch, the second latch selectively pivotable between a first position in which the second latch retains the lens with respect to the frame and a second position in which the second latch permits the lens to be removed from the frame.

13. The goggle of claim 12, wherein the first and second latches rotate between the first and second positions in opposite directions.

14. The goggle of claim 4, further comprising an over-center mechanism biasing the latch away from an intermediate position between the first and second positions and resisting movement of the latch between the first and second positions.

15. The goggle of claim 14, wherein the shaft is formed of a resilient material and pivotally mounted to the frame, and wherein the over-center mechanism includes a projection secured to the shaft and a surface secured to the frame and engaging the projection as the latch is pivoted between the first and second positions.

16. The goggle of claim 1, wherein the lower portion includes opposing slots for selectively engaging tabs formed on the lens, and wherein the lens includes first and second lenses secured to one another, the tabs being formed in a portion of the second lens extending outwardly from a perimeter of the first lens.

17. Eyewear comprising:
at least one lens having an upper perimeter and a lower perimeter, the lens defining at least one slot proximate one of the upper and lower perimeters, the lens defines an opening extending from the perimeter of the lens to the slot, the slot being wider than the opening;
a frame selectively engaging a perimeter of the lens, the frame comprising at least one of an upper portion extending across the upper perimeter and a lower portion extending across the lower perimeter; and
a fastener having a lever and mounted to the at least one of the upper and lower portions, the fastener selectively engaging the at least one slot to retain the lens in engagement with the frame by moving the lever, the fastener further having an elongate member having a first end and a second end, the second end being wider than the first end.

18. The eyewear of claim 17, wherein the elongate member is mounted on a shaft rotatably mounted to the frame, the elongate member rotatable within the slot to a crosswise position in which the slot interferes with removal of the elongate member from the slot.

19. The eyewear of claim 17, wherein the elongate member is insertable through the opening in an aligned position substantially perpendicular to the crosswise position and is not insertable through the opening in the crosswise position.

20. The eyewear of claim 19, further comprising an over-center mechanism biasing a shaft coupled to the elongate member away from an intermediate position between the aligned and crosswise positions.

21. The eyewear of claim 17, further comprising a plate secured to the elongate member, a portion of the lens positioned between the plate and the frame when the elongate member is in the crosswise position within the slot.

22. The eyewear of claim 17, wherein the lens includes first and second lenses secured to one another, the slot being formed in a portion of the second lens extending outwardly from a perimeter of the first lens.

23. The eyewear of claim 22, wherein the perimeter of the first lens is sized to fit within an inner perimeter of the frame and wherein the second lens engages a face of the frame extending outwardly from the inner perimeter.

24. The eyewear of claim 17, wherein the eyewear is a goggle.

25. The eyewear of claim 17, wherein the eyewear is sunglasses.

26. The eyewear of claim 17, wherein the slot is a first slot positioned proximate the upper perimeter of the lens and wherein the fastener is a first fastener mounted to the upper portion of the frame, the eyewear further comprising a second slot positioned proximate the lower perimeter of the lens and a second fastener mounted to the lower portion of the frame, the second fastener selectively engaging the second slot to retain the lens in engagement with the frame.

27. The eyewear of claim 17, further comprising an over-center mechanism biasing the fastener away from an intermediate position between open and closed positions, the open position permitting movement of the lens into and out of engagement with the fastener and the closed position hindering movement of the lens out of engagement with the fastener.

28. The eyewear of claim 27, wherein the elongate member is rotatable within the slot to a crosswise position in which the slot interferes with removal of the elongate member from the slot; and wherein the lens defines an opening extending from the perimeter of the lens to the slot, the slot being wider than the opening.

29. The eyewear of claim 25 wherein the frame comprises both an upper portion extending across the upper perimeter of the lens and a lower portion extending across the lower perimeter of the lens.

30. A method for assembling a goggle comprising:
latching a lower perimeter of a lens with a lower frame portion of a frame;
flexing the lower portion of the frame away from an upper frame portion of the frame;
flexing the lower frame portion toward the upper frame portion while moving an upper perimeter of the lens into engagement with a rotatable fastener secured to the upper frame portion; and
fastening the upper perimeter of the lens to the upper frame portion.

31. The method of claim 30, wherein latching the lower perimeter of the lens with the lower frame portion includes engaging tabs formed on opposing sides of a notch defined by the lens with opposing slots formed on a nose portion of the lower frame portion.

32. The method of claim 31, wherein moving the upper perimeter of the lens into engagement with a fastener includes moving the lens in an insertion direction such that an elongate member inserts within a slot defined by the lens proximate the upper perimeter, the elongate member being pivotally secured to the upper frame portion, and wherein fastening the upper perimeter of the lens to the upper frame portion comprises rotating the elongate member within the slot such that the slot interferes with relative movement of the elongate member along the insertion direction.

33. The method of claim 32, wherein flexing the lower frame portion away from the upper frame portion includes moving the upper perimeter of the lens below a plate secured to the upper frame and wherein moving the upper perimeter of the lens into engagement with a fastener further includes moving the lens between the plate and the upper frame portion.

34. The method of claim 33, wherein the plate is secured to the elongate member.

35. The method of claim 30, further comprising:
pivoting strap mounts secured to the frame;
inserting portions of the lens between the strap mounts and the frame; and
tensioning a strap secured to the strap mounts to urge the strap mounts against the lens.

36. Eyewear comprising:
a frame having at least one rotatable fastener;
a strap mount pivotally mounted to the frame;
a strap secured to the strap mount; and
a lens having an outer perimeter, the lens defining at least one slot proximate the outer perimeter, the frame being removeably secured to the lens by selectively engaging each of the at least one fastener with a respective one of the at least one slot by rotating the fastener, the lens defines an opening extending from the perimeter of the lens to the slot, the slot being wider than the opening.

37. The goggle eyewear of claim 36, wherein the strap mount includes first and second ends and an intermediate portion extending between the first and second ends, the first ends securing to the upper frame portion and the lower ends securing to the lower frame portion, the strap securing to the intermediate portion, and wherein the intermediate portions urge the lens against the frame upon tensioning of the strap.

38. The eyewear of claim 36 wherein the rotatable fastener secures the frame to the lens by rotating the fastener to a first position so that the fastener is engaged with the slot.

39. Eyewear comprising:
a frame having at least one locking mechanism, the locking mechanism including a projection mounted on a shaft rotatably mounted on the frame, the projection having a first end and a second end, the second end being wider than the first end; and
a lens having an outer perimeter, a portion of the outer perimeter of the lens defining at least one recess, the frame being locked to the lens by rotating the locking mechanism so that the projection is positioned in the recess to cause the frame to be secured to the lens, the frame being unlocked from the lens by rotating the locking mechanism so that the projection is positioned away from the frame to allow the lens to be removed from the frame.

40. The eyewear of claim 39 wherein the recess comprises a slot.

41. The eyewear of claim 39 wherein the lens is a single lens.

42. The eyewear of claim 39 wherein the eyewear is a goggle with a goggle frame and a goggle lens.

* * * * *